United States Patent [19]
Nemoto

[11] Patent Number: 5,556,529
[45] Date of Patent: Sep. 17, 1996

[54] DNA BASE SEQUENCER

[75] Inventor: Ryozi Nemoto, Honzyo, Japan

[73] Assignee: Hitachi Electronics Engineering Co., Ltd., Tokyo, Japan

[21] Appl. No.: 500,204

[22] Filed: Jul. 10, 1995

[30] Foreign Application Priority Data

Jul. 13, 1994  [JP]  Japan .................................. 6-183028

[51] Int. Cl.$^6$ .......................... G01N 27/26; G01N 27/447
[52] U.S. Cl. .......................... 204/612; 204/461; 204/466; 204/467; 204/616; 204/618; 356/344
[58] Field of Search ........................... 204/299 R, 182.8, 204/180.1; 356/344

[56] References Cited

U.S. PATENT DOCUMENTS

| | | | |
|---|---|---|---|
| 5,062,942 | 11/1991 | Kambara et al. | 356/344 X |
| 5,162,654 | 11/1992 | Kostichka et al. | 250/458.1 |
| 5,290,419 | 3/1994 | Kambara et al. | 204/182.8 X |
| 5,307,148 | 4/1994 | Kambara et al. | 356/344 |

FOREIGN PATENT DOCUMENTS

| | | |
|---|---|---|
| 459278 | 12/1991 | European Pat. Off. . |
| 626578 | 11/1994 | European Pat. Off. . |
| 645622 | 3/1995 | European Pat. Off. . |

OTHER PUBLICATIONS

Bruno et al, "The Pigtailing Approach to Optical Detection in Capillary Electrophoresis", TrAC: Trends in Analytical Chemistry, vol. 13, No. 5, May 1994, pp. 190–198.

*Primary Examiner*—John Niebling
*Assistant Examiner*—John S. Starsiak, Jr.
*Attorney, Agent, or Firm*—Fay, Sharpe, Beall, Fagan, Minnich & McKee

[57] ABSTRACT

The improved DNA base sequencer has a flat plate type gel electrophoretic unit that has multiple tracks for electrophoresing DNA fragments and which is held in a vertical position, a light exciting laser light applying unit that applies laser light to the respective tracks in the electrophoretic unit from one lateral side thereof in such a way that it crosses the tracks at right angles, and a fluorescence detecting unit that detects the fluorescence as generated from the DNA fragments illuminated with the laser light and which converts the detected fluorescence to an electric signal. The sequencer is characterized in that the fluorescence detecting unit comprises a fluorescence condensing lens, a fluorescence filtering unit and a solid-state imaging device, (e.g., a CCD line sensor), the fluorescence filtering unit being composed of at least two filters that selectively transmit fluorescences having different wavelengths and that are staggered with each other along a common longitudinal axis. The sequencer achieves a sensitivity and resolution at least comparable to those attained by the prior art apparatus and yet which is capable of detecting multi-color labelled samples by means of simpler detection optics.

6 Claims, 8 Drawing Sheets

5,556,529

DNA BASE SEQUENCER

BACKGROUND OF THE INVENTION

This invention relates to a DNA base sequencer, or an apparatus for determining the base sequences of DNA. More particularly, this invention relates to an apparatus with which the base sequences of DNA can be determined with a plurality of fluorescence markers in an efficient and rapid manner.

Gel electrophoresis is practiced extensively as a technique for determining the base sequences of DNA and other proteins. Conventionally, the sample to be subjected to electrophoresis is labelled with a radioisotope for analysis but this method has had the problem of being painstaking and time-consuming. Furthermore, the use of radioactive substances always calls for utmost safety and management and analysis cannot be performed in areas other than facilities that clear certain regulations. Under the circumstances, a method that uses fluorophores to label the sample and which detects fluorescences as emitted upon irradiation with light is being reviewed.

In this method, fluorophore-labelled DNA fragments are caused to migrate through a gel, and a light excitation portion and a photodetector are provided for each electrophoresis track in an area 5–20 cm below the start point of electrophoresis. The DNA fragments are assayed as they pass through the line connecting the light excitation portion and the photodetector. A typical procedure of the method is described below. First, using as a template the DNA chain to be determined for its base sequence, DNAs of various lengths with known terminal base species are replicated by a method involving an enzymatic reaction (the dideoxy method). Then, the replicated DNAs are labelled with a fluorophore. Stated more specifically, there are prepared a group of adenine (A) fragments, a group of cytosine (C) fragments, a group of guanine (G) fragments and a group of thymine (T) fragments, all being labelled with a fluorophore. A mixture of these fragment groups is injected into separate lane grooves in an electrophoretic gel and, thereafter, a voltage is applied at opposite ends of the gel. Since DNA is a chained polymer with negative charges, it will move across the gel at a rate in inverse proportion to its molecular weight. The shorter the DNA chain (the smaller its molecular weight), the faster will it move and vice versa; this is the principle behind the fractionation of DNA by molecular weight.

With a view to analyzing a greater number of samples on an electrophoresis plate having a limited width, DNA base sequencers have been developed that share a common lane for electrophoresing a plurality of samples (e.g. bases) labelled with different fluorescent dyes so that they can be detected by differentiation with the initial color labels.

An example of such apparatus is shown in FIG. 13. An electrophoresis plate 74 comprises a gel (typically a polyacrylamide gel) held between two glass plates. The electrophoresis plate has an overall thickness of up to about 10 mm but the thickness of the gel electrolyte layer itself is less than about 1 mm. The upper end of the gel electrolyte layer is comb-shaped and located slightly below the upper end of the plate 74. DNA fragments labelled with a plurality of fluorophores (e.g. producing two colors) are injected into grooves 75 corresponding to the teeth of the comb.

In the apparatus shown in FIG. 13, a laser beam emitted from a light source 70 is launched horizontally from one side of the plate 74 at a predetermined point on the gel. As the fluorophore-labelled DNA fragments migrating through the gel pass through the irradiated region, they will fluoresce successively. The horizontal position of fluorescence emission tells the species of a particular terminal base, the time difference from the start of migration tells the length of a particular fragment, and the emission wavelength identifies the sample under assay. A prism 92 is provided adjacent and close to tête-à-tête a principal surface of the electrophoresis plate; a filter 94 composed of an upper and a lower segment is provided adjacent the prism 92; sensor A 96a for receiving fluorescence at one wavelength (λ1) and sensor B 96b for receiving fluorescence at another wavelength (λ2) are provided behind the filter 94; and an imaging lens 98 is provided between the filter 94 and the sensor array. Shown by 100 and 102 in FIG. 13 are an upper buffer tank and a lower buffer tank, respectively.

FIG. 14 shows schematically the principle for differentiating fluorescence of one color from fluorescence of another color. FIG. 15 shows characteristic curves for the fluorescence intensities of two markers, one emitting fluorescence at wavelength λ1 and the other emitting fluorescence at wavelength λ2. FIG. 16 shows corresponding characteristic curves for the fluorescence intensities as obtained after transmission through the filters. Turning back to FIG. 14, if sample 76 labelled with a fluorescent dye emitting at wavelength λ1 crosses a point of emission, fluorescence will be generated that has the intensity shown in FIG. 15. The emitted fluorescence at wavelength λ1 is launched into prism 92, refracted by it and admitted into filter A 94a for receiving fluorescence at wavelength λ1 and filter B 94b for receiving fluorescence at wavelength λ2. The fluorescence at wavelength λ1 that has been admitted into filter B 94b is cut off and incapable of transmission through this filter. Therefore, the fluorescence at wavelength λ1 that has passed through filter A 94a is focused by the imaging lens 98 to form an image on sensor A 94a for subsequent detection. The fluorescence having passed through filter A 94a has substantially the same transmittance as the fluorescence having passed through filter B 94b (see FIG. 16).

The apparatus described above has various drawbacks such as the complexity of the optics, the need to employ more than one sensor, and the lower intensity of fluorescence due to light separation by the prism.

FIG. 17 shows another known example of the DNA base sequencer that employs labelling with two fluorescent dyes emitting at different wavelengths. In the apparatus, a light source 70 positioned in front of an electrophoresis plate 74 emits laser light 90 toward a labelled sample 76 and the resulting fluorescence is received on the same side of the electrophoresis plate. The fluorescence passes through a disk-shaped filter 104 consisting of two segments and is focused by an imaging lens 106 to form an image on a photomultiplier 108. Since the disk-shaped filter 104 is rotating, fluorescence at wavelength λ1 passes through the filter alternately with fluorescence at wavelength λ2. FIG. 18 is a timing chart illustrating how the two fluorescences emitting at wavelengths λ1 and λ2 are detected by means of the rotating filter 104.

A problem with the apparatus shown in FIG. 17 is that it requires a mechanism for rotating the filter and, hence, involves a complicated construction. In addition, all electrophoresis lanes are detected by scanning the entire part of the optics but, then, the detection speed is unavoidably slow because the number of revolutions of the filter has to satisfy a certain relationship with the timing of scanning.

SUMMARY OF THE INVENTION

The present invention has been accomplished under these circumstances and has an object of providing a DNA base sequencer that achieves a sensitivity and resolution at least comparable to those attained by the prior art apparatus and which yet is capable of detecting multi-color labelled samples by means of simpler detection optics.

This object can be attained by a DNA base sequencer comprising a flat plate type gel electrophoretic means that has multiple tracks for electrophoresing DNA fragments and which is held in a vertical position, a light-exciting laser light applying means that applies laser light to the respective tracks in said electrophoretic means from one lateral side thereof in such a way that it crosses said tracks at right angles, and a fluorescence detecting means that detects the fluorescence as generated from the DNA fragments illuminated with the laser light and which converts the detected fluorescence to an electric signal, characterized in that said fluorescence detecting means comprises a fluorescence condensing lens, fluorescence filtering means and a solid-state imaging device, said fluorescence filtering means being composed of at least two filters that selectively transmit fluorescences having different wavelengths and that are staggered with each other along a common longitudinal axis.

Fluorescences having different wavelengths pass only the filters that have the associated transmittances and, hence, one sensor will suffice to achieve effective detection of each fluorescent light.

THE PREFERRED EMBODIMENTS OF THE INVENTION

The present invention is described below in greater detail with reference to FIGS. 1–12.

Figure 1:
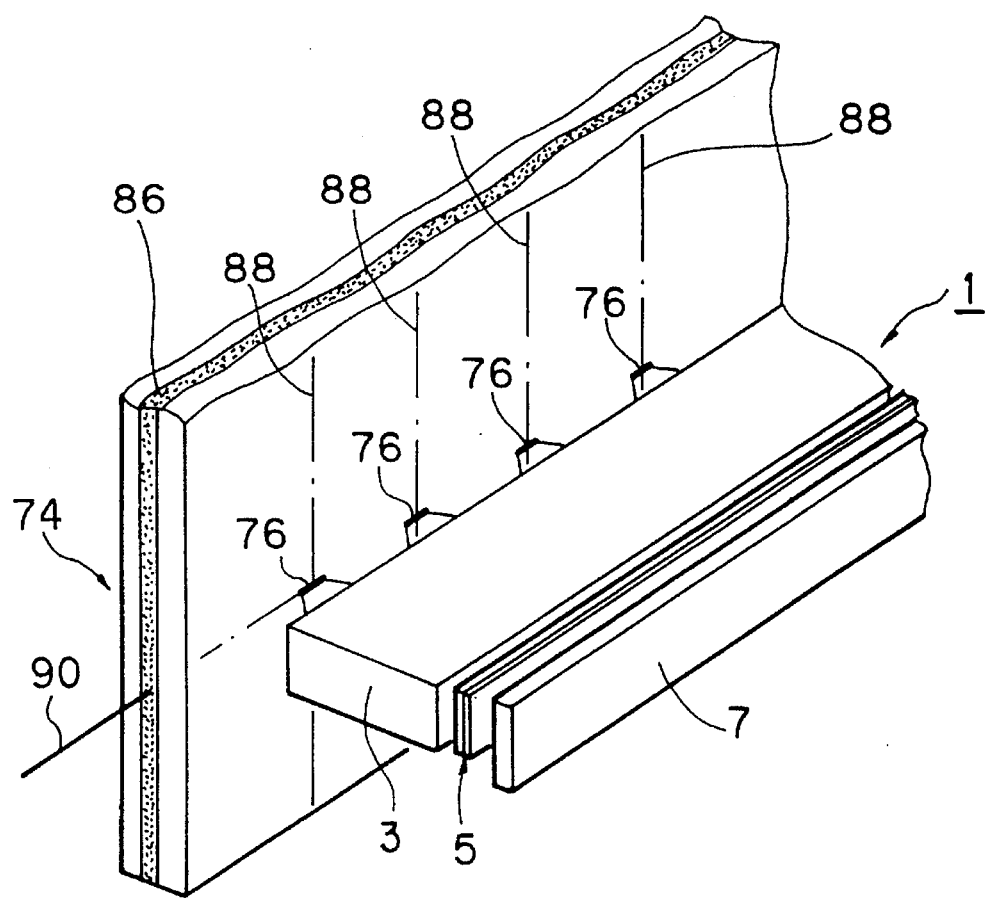
FIG. 1 is a perspective view showing schematically the partial structure of the fluorescence detecting means used with the DNA base sequencer of the invention.

FIG. 1 is a perspective view showing schematically the partial structure of fluorescence detecting means that is used with the DNA base sequencer of the invention and which is generally indicated by reference numeral 1. The fluorescence detecting means consists basically of an index-distributed lens array 3, fluorescence filtering means 5 in the form of two superposed filters, and a solid-state imaging device such as a CCD (charge-coupled device) line sensor 7. DNA fragments 76 are migrating downward along respective electrophoresis tracks 88 on a gel electrolyte layer 86 in an electrophoresis plate 74; when they are illuminated with laser light 90 from one lateral side of the gel electrolyte layer, fluorescence is emitted from the illuminated DNA fragments. The emitted fluorescence is launched into the index-distributed lens array 3 and passes through it to enter the filter 5, which cuts off the background light or any stray light that has wavelengths other than those of the fluorescent components. The fluorescent light that has passed through the filter is picked up by the CCD line sensor 7 for conversion to electric signals. In addition to the CCD line sensor, a MOS transistor array or a photodiode array may also be used as the solid-state imaging device with equal results.

Figure 2:
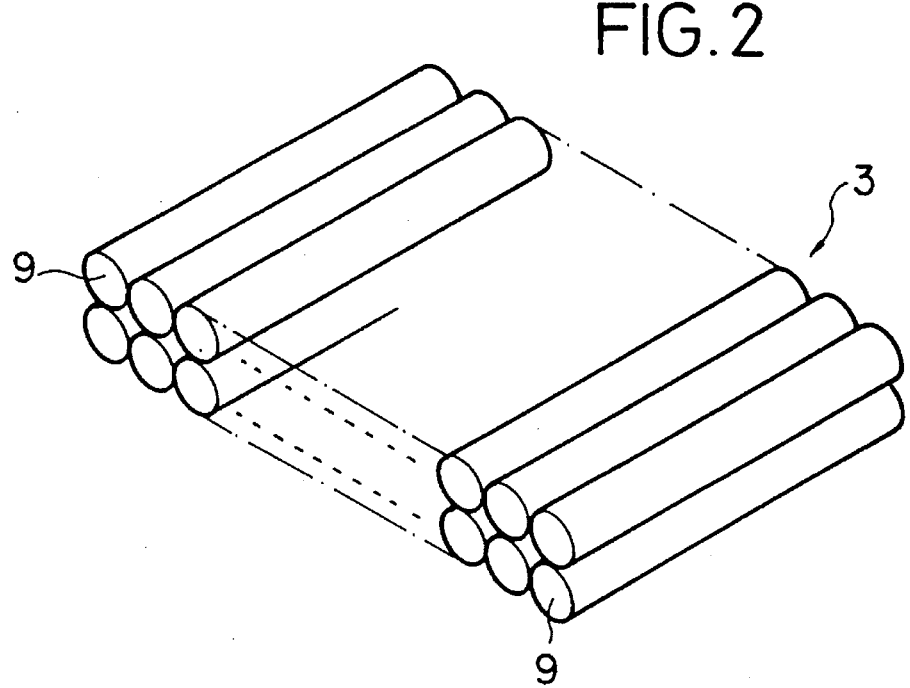
FIG. 2 is an enlarged perspective view showing schematically the index-distributed lens array for use in the invention as part of the fluorescence detecting means.

FIG. 2 is an enlarged perspective view showing schematically the index-distributed lens array 3. Each of the index-distributed lenses 9 used in the invention is also known as a "Selfoc lens" which is a cylindrical lens having a refractive index distribution in the radical direction. If the index-distributed lens array is in close proximity with the electrophoresis plate for focusing a fluorescent image, uniform signal levels are attained between the center and either end of the plate. As a result, the uniformity of S/N ratio is improved and one can read of the length of bases in lanes in the marginal portions of the plate as precisely as in lanes at the center and nearby areas. If index-distributed lenses are disposed in an array, adjacent lens images will overlap, whereby 1:1 erecting imaging optics are provided in the lens mounting area.

The "Selfoc lens" to be used in the invention is commercially available under code number SLA-20B (FO. 96) and has a diameter of about 1 mm with a length of about 12–13 mm. Selfoc lenses can be used as a single-row array. In the embodiment shown in FIG. 2, the lens array 3 consists of an upper and a lower row, each being composed of 200 lenses amounting to a total of 400 lenses. The Selfoc lenses are arrayed in two rows for the purpose of achieving a higher resolution by allowing more light to be accepted by the lenses. If the Selfoc lenses are arrayed in two rows, the numerical aperture of the lens optics is increased to enable the detection of weak fluorescence. If desired, Selfoc lenses may be stacked in three or more rows. Needless to say, lenses 9 are supported by a suitable enclosure or retainer so that they are held together in the form of lens array 3. In the invention, conventional camera lenses may be substituted for the Selfoc lenses.

Figure 3:
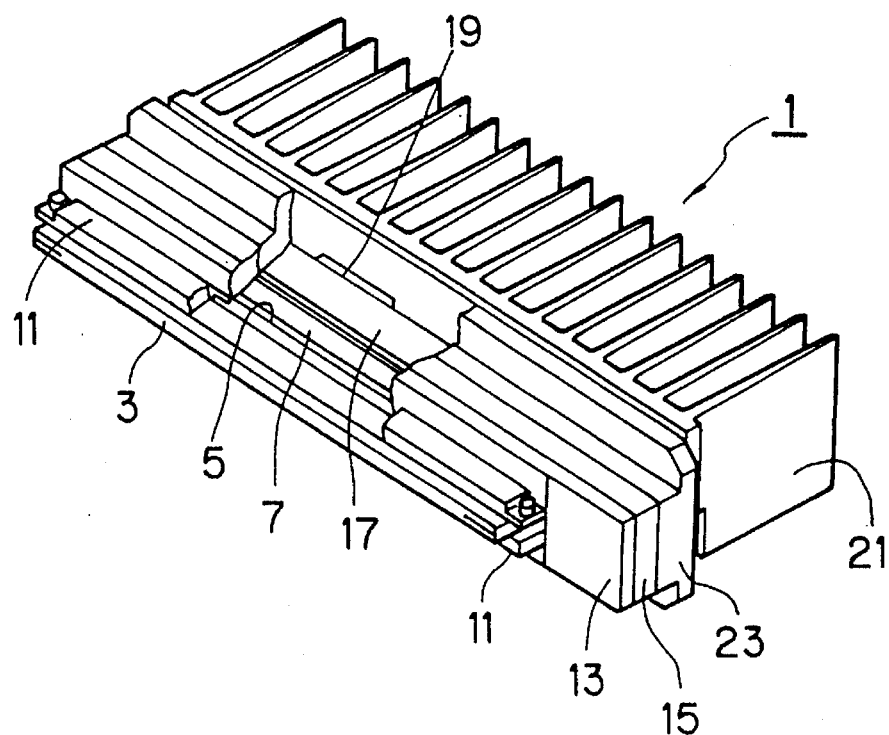
FIG. 3 is a perspective view showing, with part taken away, an example of the assembly of the fluorescence detecting means shown in FIG. 1.

FIG. 3 is a perspective view showing, with part taken away, an example of the assembly of the fluorescence detecting means 1 shown in FIG. 1. As shown in FIG. 3, the index-distributed lens array 3 is held between suitable fixing plates 11. One of the fixing plates 11 is secured to a filter mount 13, in which the two superposed filters 5 are installed. Adjacent to and in close contact with the filter mount 13, there is provided a CCD mount 15, in which the CCD line sensor 7 is disposed. When driven, the CCDs generate heat and the dark current will increase to produce noise, causing adverse effects such as a reduced S/N ratio. To avoid these problems, a uniform heating zone 17 is provided in contact with the CCD line sensor 7 and an electric cooler/heater 19 such as a Peltier device is provided in contact with the heating zone 17. The CCD line sensor is preferably maintained at a temperature within the range from about 10° C. to about 15° C. by means of the Peltier device 19. A heat sink 21 is secured to the electronic cooler/heater 19 so as to improve its heat dissipation characteristics. The heating zone 17 and the electronic cooler/heater 19 are both held by means of a cooling mount 23. As is generally the case, the CCDs are mounted on a CCD substrate or board but this portion is omitted from FIGS. 3 and 4 for clarity.

Figure 4:
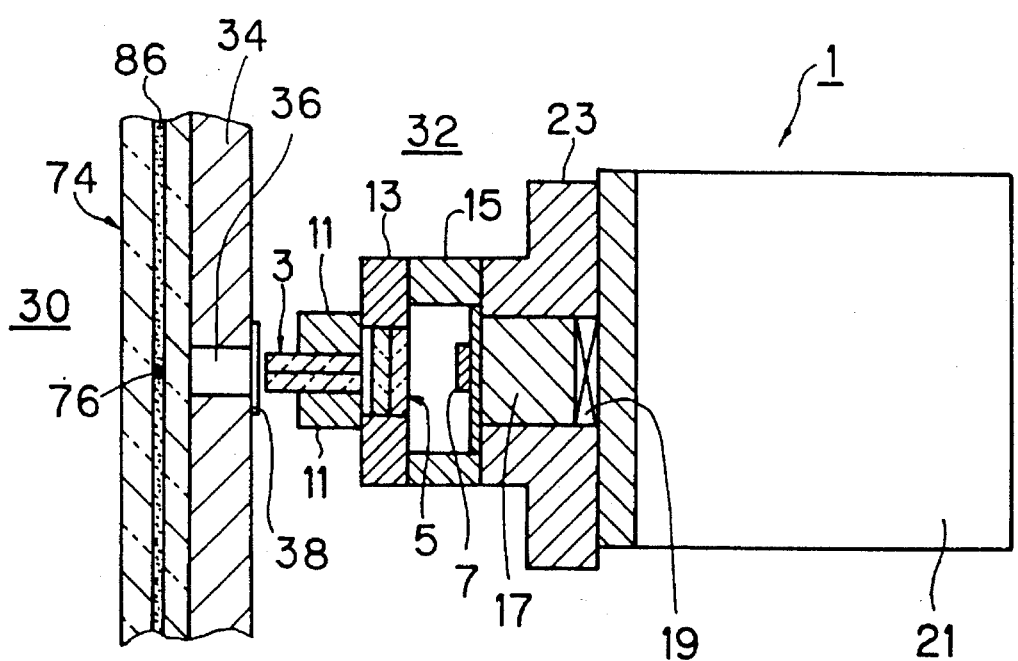
FIG. 4 is a sectional view showing schematically the fluorescence detecting means assembly of FIG. 3 as it is mounted on the DNA base sequencer.

A further discussion is made with reference to FIG. 4, which is a sectional view showing schematically the fluorescence detecting means assembly 1 of FIG. 3 as it is mounted in the DNA base sequencer. The DNA base sequencer of the invention comprises basically a dark compartment 30 containing the electrophoresis plate 74 and a measurement compartment 32 containing the fluorescence detecting means assembly 1. The dark compartment 30 is separated from the measurement compartment 32 by a partition 34. The partition 34 has an opening 36 in the position corresponding to the point of entrance of laser light into electrophoresis plate 74 so that excited fluorescence is effectively guided toward the measurement compartment 32. An airtigtness providing glass plate 38 is secured to the end of the opening 36 where it faces the measurement compartment 32 in order to assure that the moisture or heat in the dark compartment 30 will not enter the measurement compartment through the opening. The electrophoresis plate 74 is detachable and retained in a vertical erect position so that it makes close contact with the partition 34.

The distance from the point of incidence of laser light 76 on the electrophoresis plate 74 to the front end of the Selfoc lens array is not limited to any particular value but a value of about 15 mm is selected in the embodiment under discussion. The distance from the rear end of the Selfoc lens array to the surface of the CCD line sensor 7 also is not limited to any particular value but a value of about 15 mm is selected in the embodiment under discussion. The distance from the point 76 to the front end of the Selfoc lens array may or may not be the same as the distance from the rear end of the Selfoc lens array to the surface of the CCD line sensor 7. Preferably, the two distances are the same because Selfoc lenses which have a magnification of unity are preferably provided with the same volume of gaps both ahead and behind the lenses.

Figure 5:
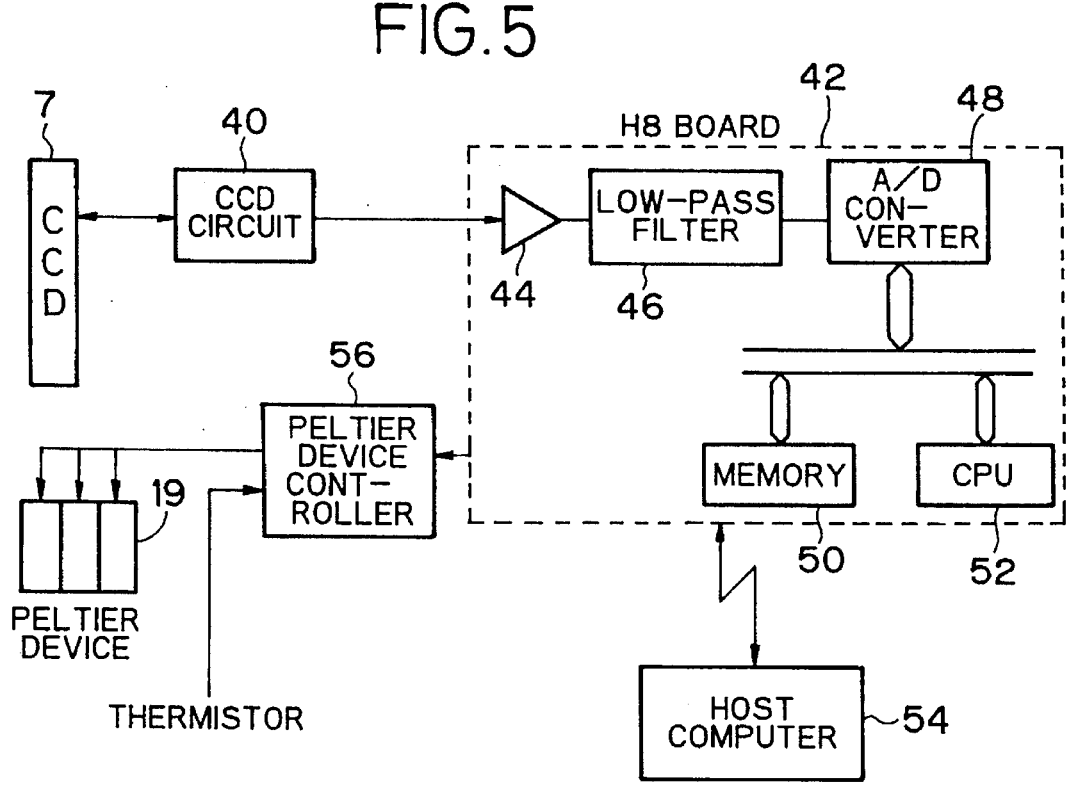
FIG. 5 is a block diagram of a signal processing system including a CCD circuit.

FIG. 5 is a block diagram of a signal processing system including a CCD line sensor 7 that is driven with the CCD circuit indicated by reference numeral 40. The contents of the CCD circuit 40 are essentially the same as those of a known conventional CCD drive circuit and comprise a timing controller, a timing generator circuit, a multiplexer, etc. An analog output as received by the CCD line sensor 7 and subsequently processed in the CCD circuit 40 is supplied to an H8 board 42. This analog output is amplified by an amplifier 44, filtered through a low-pass filter 46 for rejection of the noise component and converted to a digital signal in an A/D converter 48. The digital signal is then processed with an arithmetic operation processing system comprising a memory 50 and a CPU 52. The H8 board may optionally be connected to a host computer 54. The H8 board 42 also serves as an I/O interface with a Peltier device controller 56. In response to a signal from a thermistor (not shown), the Peltier device controller 56 performs an on-off control over the drive of Peltier devices 19. The CCD circuit may contain a circuit for integrating pixel signals from CCDs. This integrating circuit not only reduces noise but also enables pixel adjustment in the following manner: consider, for example, the case where a CCD produces an output of 63.5 μm/pix; this output is integrated over 4 pixels to give 254 μm/pix, which is delivered as an adjusted CCD output.

The index-distributed lens array 3, filter 5 and CCD line sensor 7 preferably have the same length. Their lengths may be the same as the lateral width of the electrophoresis plate 74, or the distance from the left to the right end of the plate 74; alternatively, their length may be slightly shorter than the lateral width of the electrophoresis plate so as to be equal to the distance from the electrophoresis track at the right end to the track at the left end plus an allowance for "smiling".

CCD line sensor 7 has a plurality of CCDs arranged side by side in a linear fashion and is also used in the photoelectric transducer portion of scanning optics in OCRs or facsimiles. The CCDs to be used in the invention are not limited to any particular types and TCD 109AC (pixel size: 65 ×65 μm) may be used with advantage. The distance between the upper and lower edges of the CCD line sensor (namely, the width as measured in the electrophoresing direction) is not limited to any particular value; however, values no more than 85 μm are generally preferred. In the early stage of electrophoresis, DNA fragments separate sharply enough to facilitate their detection but toward the end of electrophoresis, the separability of DNA fragments decreases progressively until they migrate collectively. If the distance between the upper and lower edges of the CCD line sensor is not more than 85 μm, DNA fragments can be detected individually even if they migrate collectively. If only one CCD line sensor is used, it functions as a one-dimensional sensor; on the other hand, if two or more CCD line sensors are stacked in a corresponding number of rows, a two-dimensional area sensor is realized.

Figure 6:
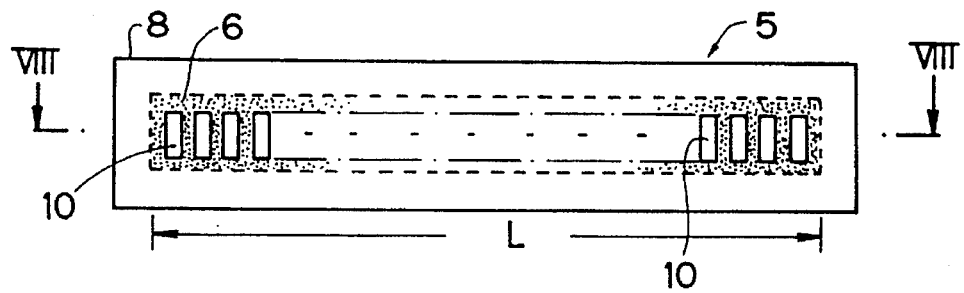
FIG. 6 is a front view of an example of the filter for use in the fluorescence detecting means.
Figure 7:
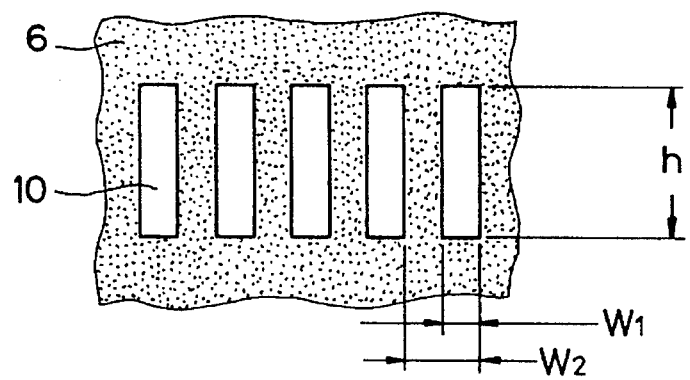
FIG. 7 is a partial enlarged view of the filter shown in FIG. 6.
Figure 8:
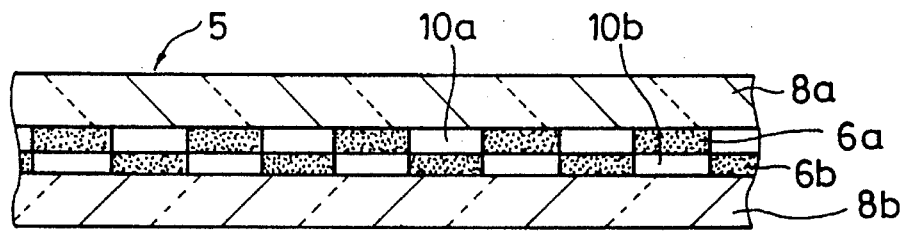
FIG. 8 is a cross section taken on line VIII—VIII of FIG. 6.

FIG. 6 is a front view of an example of the filter 5 which is to be used in the apparatus of the invention. FIG. 7 is an enlarged view of the thin-film portion serving as the filter. FIG. 8 is a cross section taken on line VIII—VIII of FIG. 6. Filter 5 is typically formed by providing a thin film 6 capable of selective transmission of light on one side of a transparent glass plate 8. The length L of the thin-film portion is variable with the type of the apparatus with which the filter is to be used and is typically 190 mm. Given this value of L, the glass plate 8 has an overall length of 194 mm, a height of 12 mm and a thickness of 2 mm.

As FIGS. 6 and 7 show, thin film 6 has windows 10 formed by removing selected areas thereof by a suitable method such as etching. Each window has a width W1 of, for example, 254 μm, and the spacing W2 between adjacent windows is preferably twice W1. The height of each window, h, is not limited to any particular value but is preferably about 3 mm.

As FIG. 8 shows, filter 5 is typically formed of two transparent glass plates 8a and 8b with thin films 6a and 6b, respectively, that are superposed in such a way that the thin films face each other. The thin film 6a on the glass plate 8a is capable of selectively transmitting light at a specified wavelength whereas the thin film 6b on the glass plate 8b is capable of selectively transmitting light at another wavelength. When superposing the two glass plates, care must be taken that windows 10a are staggered with respect to windows 10b so that the former will not overlap the latter. If this requirement is met, fluorescence can be transmitted through both thin films 6a and 6b.

It should be noted here that the invention is in no way limited to the particular embodiment in which the glass plates are superposed in such a way that the thin film on one glass plate will face the thin film on the other glass plate. Other embodiments are possible as long as the windows in one glass plate are staggered with respect to the windows in the other glass plate; thus, the two glass plates may be superposed in such a way that the thin film is positioned on the outer surface of each glass plate, or that the thin film on one glass plate is positioned on the outer surface whereas the thin film on the other glass plate is positioned on the inner surface. Preferably, the two glass plates are superposed in such a way that the thin film on one glass plate will face the thin film on the other glass plate because the distance of travel of fluorescence from a Selfoc lens to the thin film on one glass plate is substantially equal to the distance from the Selfoc lens to the thin film on the other glass plate.

The thin films for transmitting fluorescence may be selected as appropriate to the kinds of fluorescence markers and laser light source (i.e., the wavelength of laser light) used. If an argon laser is used as the laser light source, it emits laser light at a wavelength of about 488 nm. If FITC (fluorescein isothiocyanate) is used as a fluorophore for labeling DNA fragments, upon illumination with the laser light having the above-mentioned wavelength, FITC emits fluorescence at a wavelength of about 515 nm. If TMRITC (tetramethylrhodamine isothiocyanate) is used as a fluorescence marker, it will emit fluorescence at a wavelength of about 570 nm upon illumination with the same laser light. Hence, the filtering thin film 6a is preferably of a type that transmits only the fluorescence having the wavelength 515 nm while rejecting the fluorescence, stray light or background light that have wavelengths other than 515 nm, whereas the filtering thin film 6b is preferably of a type that transmits only the fluorescence having the wavelength 570 nm while rejecting the fluorescence, stray light or background light that have wavelengths other than 570 nm. Exciting laser light may be emitted from a single light source common to the respective fluorescent dyes; alternatively, separate light sources may be employed that have excitation wavelengths optimal for the individual fluorescent dyes.

An example of such a fluorescence filtering thin film 6 is a dielectric multi-layered film that may be produced by any known method. Windows 10 may also be formed by customary techniques such as etching. When producing a dielectric multi-layered film that is capable of transmitting fluorescences at the respective wavelengths of interest, the distance between adjacent thin films and thin-film layers should be adjusted to optical pathlengths adapted to the respective wavelengths. Several micrometers will suffice as the thickness of the thin film per se.

Figure 9:
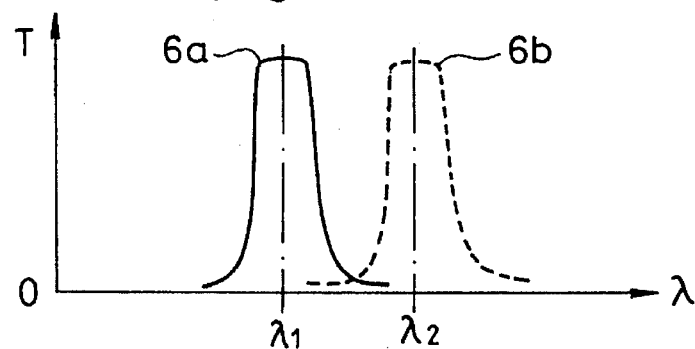
FIG. 9 is a characteristic diagram showing the transmittances of light that has passed through the fluorescence filtering thin films shown in FIG. 8.

FIG. 9 is a characteristic diagram showing the wavelength vs transmittance profile for each of the thin films 6a and 6b. As shown, each thin film transmits only the fluorescence having the associated wavelength and the two thin films have preferably the same transmittance of fluorescence.

Figure 10:
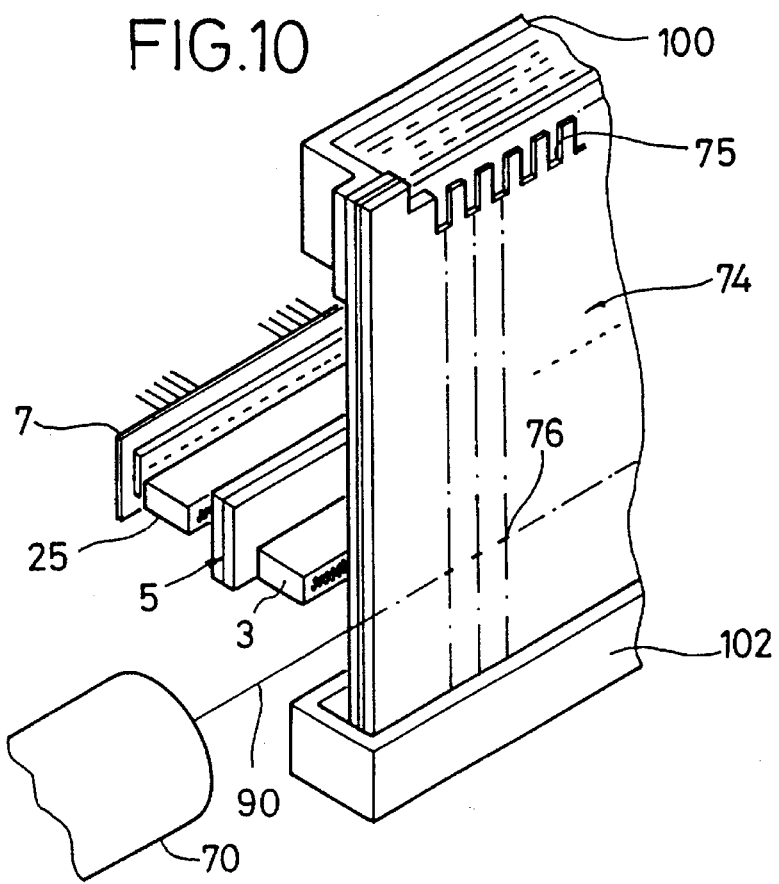
FIG. 10 is a perspective view showing schematically the partial structure of another example of the fluorescence detecting means used with the DNA base sequencer of the invention.

FIG. 10 is a perspective view showing schematically the partial structure of another example of the fluorescence detecting means used with the DNA base sequencer of the invention. The difference from the example shown in FIG. 1 is that an additional Selfoc lens array 25 is provided between the filter 5 and the CCD sensor 7. The Selfoc lens array 3 provided ahead of the filter 5 and the Selfoc lens array 25 provided behind the filter 5 insure that color separation is positively accomplished at the imaging position. If desired, filter 5 may be provided just ahead of the imaging face of the CCD sensor but a problem with this arrangement is that the efficiency of color separation may occasionally deteriorate because it is performed on samples that are not in focus.

Figure 11:
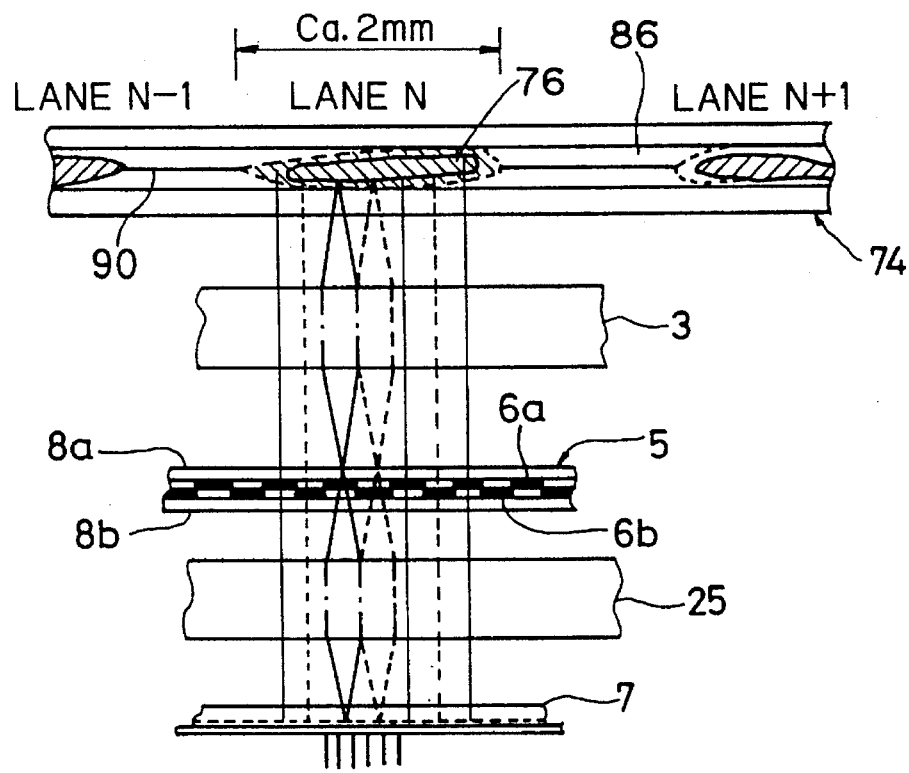
FIG. 11 is a section showing schematically how fluorescence is detected by the fluorescence detecting means shown in FIG. 10.

FIG. 11 shows schematically how fluorescence is detected by means of the fluorescence detecting means used with the apparatus shown in FIG. 10. An electrolyte layer 86 contains a plurality of electrophoresis lanes each having a width of about 2 mm and DNA bases migrate downward along these lanes in a substantially vertical direction. In lane N, a fluorescence labelled base is illuminated at a specified position 76 with a laser beam 90 coming from a lateral side of the electrophoresis plate 74, whereupon fluorescence is emitted and radiated forward, or ahead of the electrophoresis plate 74. The radiated fluorescence is admitted into the first Selfoc lens array 3, which allows it to form an image on the filtering thin film 6a or 6b in the filter 5, whereas only the fluorescence having a specified wavelength passes through the associated thin film to be admitted into the second Selfoc lens array 25, which allows the filtered fluorescence having the specified wavelength to form an image on each of the devices in the CCD sensor 7.

As already mentioned, each of the frames defined by windows 10 in the filtering thin film 6a or 6b has a size of 254 μm, which is sufficiently smaller than the lane width which is 2 mm. This insures that the fluorescence emitted from each lane to enter the Selfoc lens array is positively focused on the filtering thin film 6a or 6b. The CCD sensor 7 used in the example under consideration has a total of about 1728 pixels. Each of the pixels in the CCD must be of such a size that the transmissive width of each filtering thin film can be divided by an integer, say, four. This means the size of a pixel is 63.5 μm if one frame in the filtering thin film has a width of 254 μm.

Figure 12:
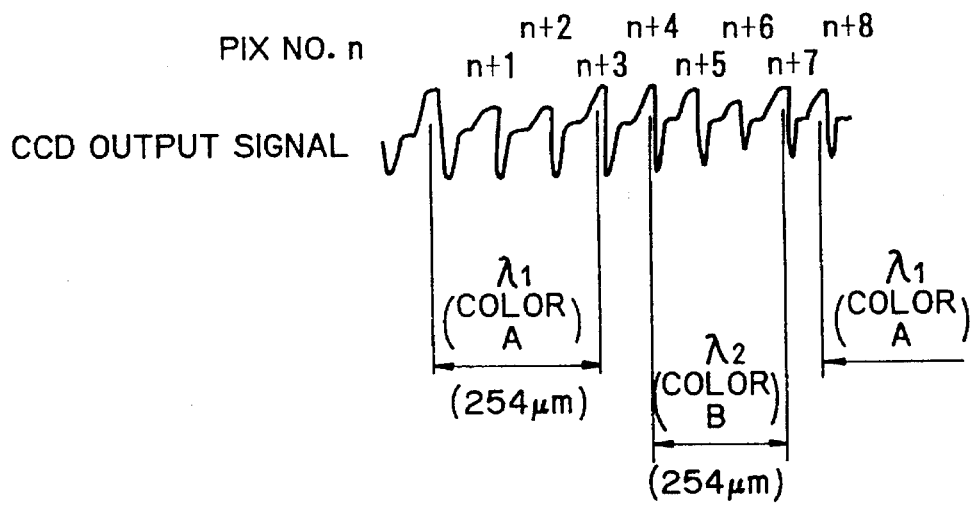
FIG. 12 shows the waveform of an output signal from a CCD line sensor.
Figure 13:
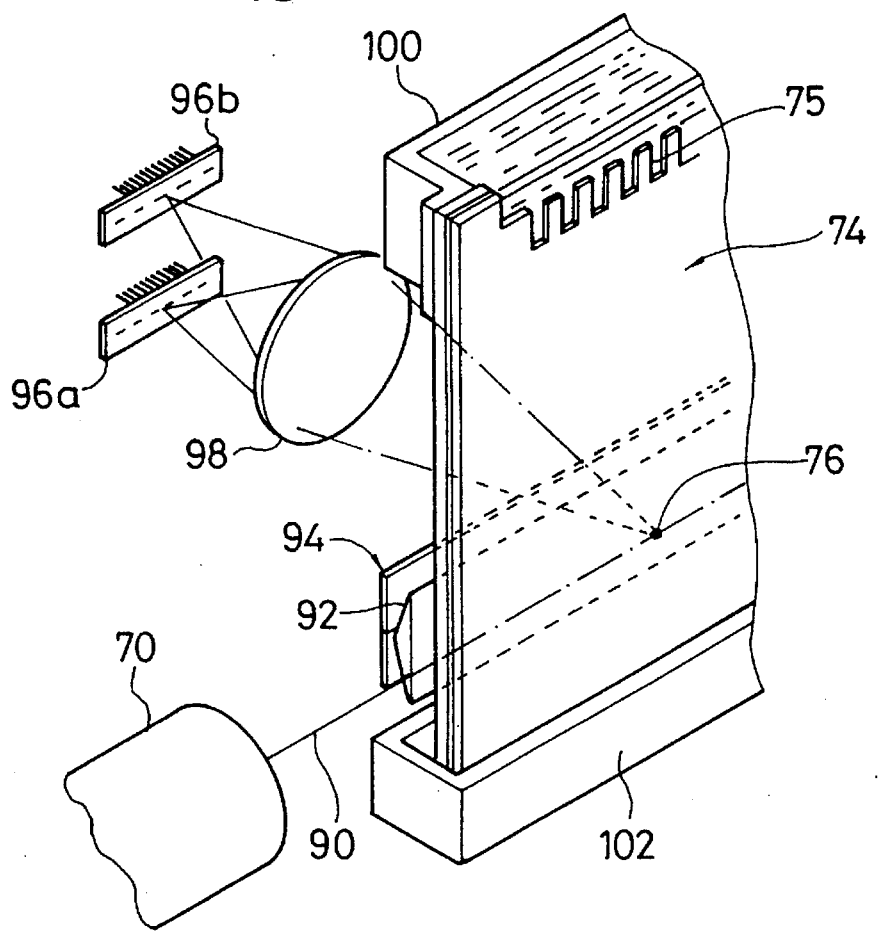
FIG. 13 is a perspective view showing schematically the partial structure of the fluorescence detecting means used with a prior art dichromatic DNA base sequencer.
Figure 14:
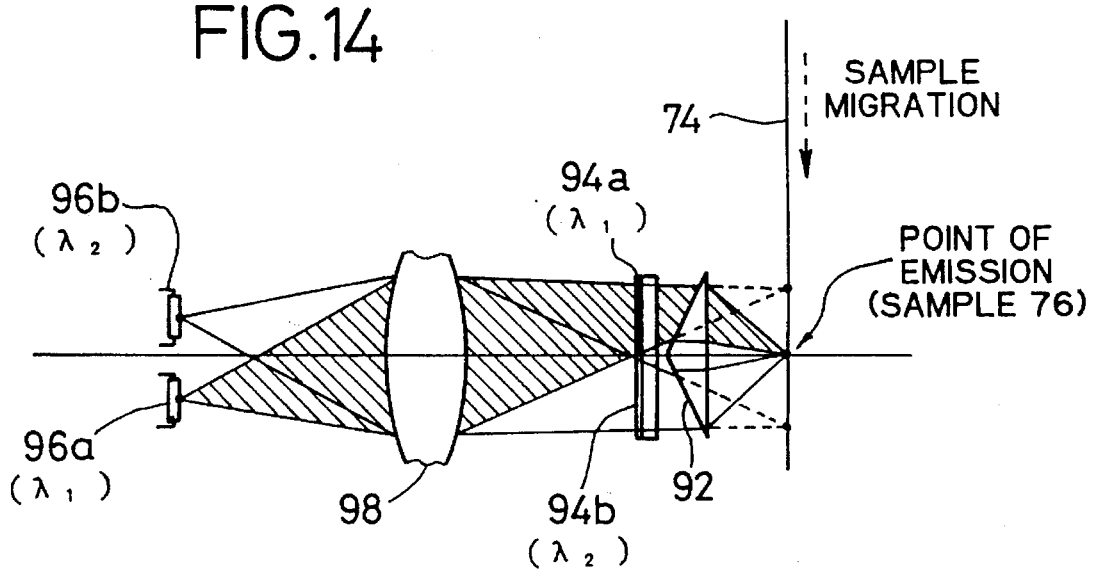
FIG. 14 is a partial section showing schematically the principle for detecting fluorescence by the fluorescence detecting means shown in FIG. 13.
Figure 15:
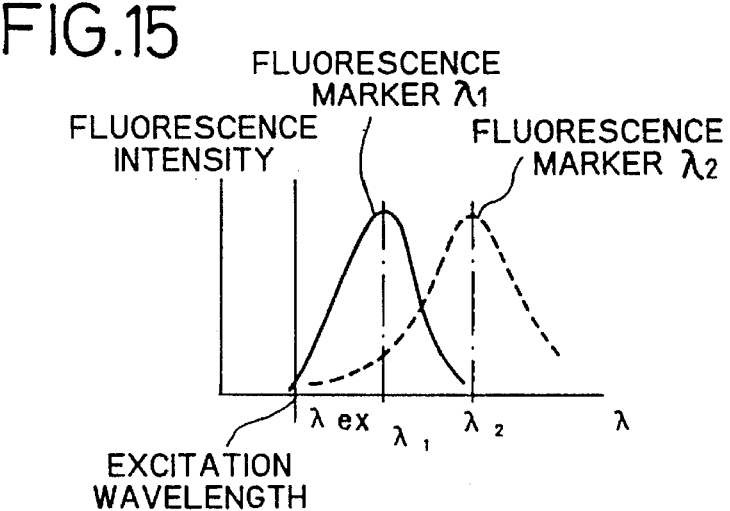
FIG. 15 is a characteristic diagram showing the intensity of fluorescence from each of the fluorescence markers as they cross the point of emission shown in FIG. 14.
Figure 16:
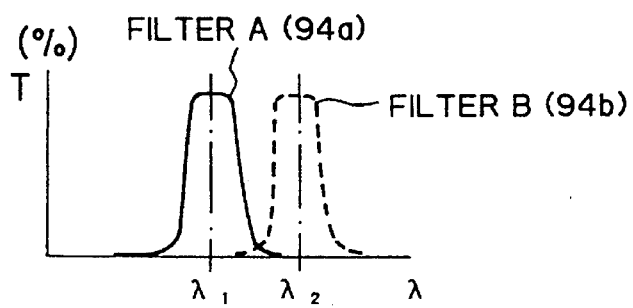
FIG. 16 is a characteristic diagram showing the transmittances of fluorescences as they pass through the filters shown in FIG. 14.
Figure 17:
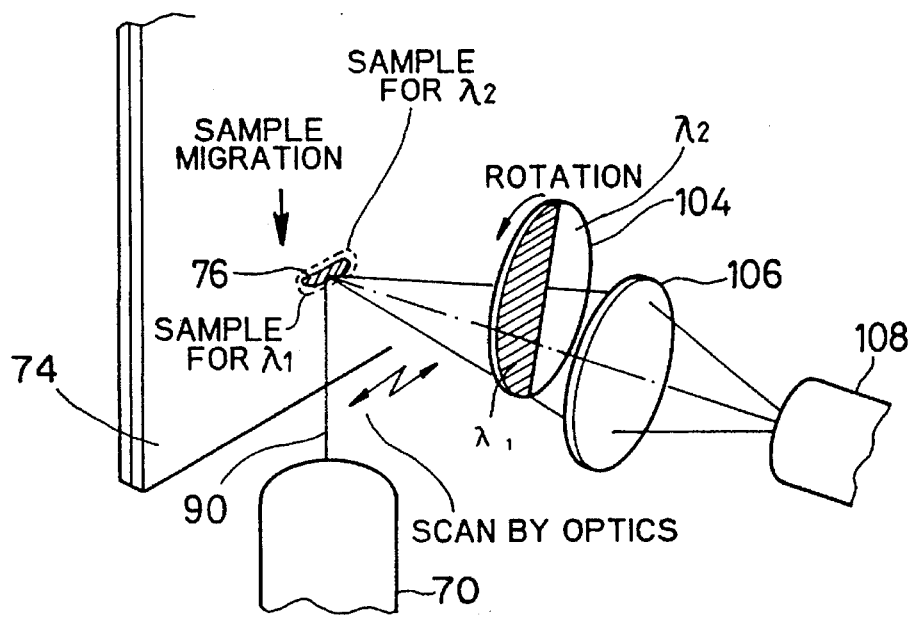
FIG. 17 is a perspective view showing schematically the partial structure of the fluorescence detecting means used with another prior art dichromatic DNA base sequencer.
Figure 18:
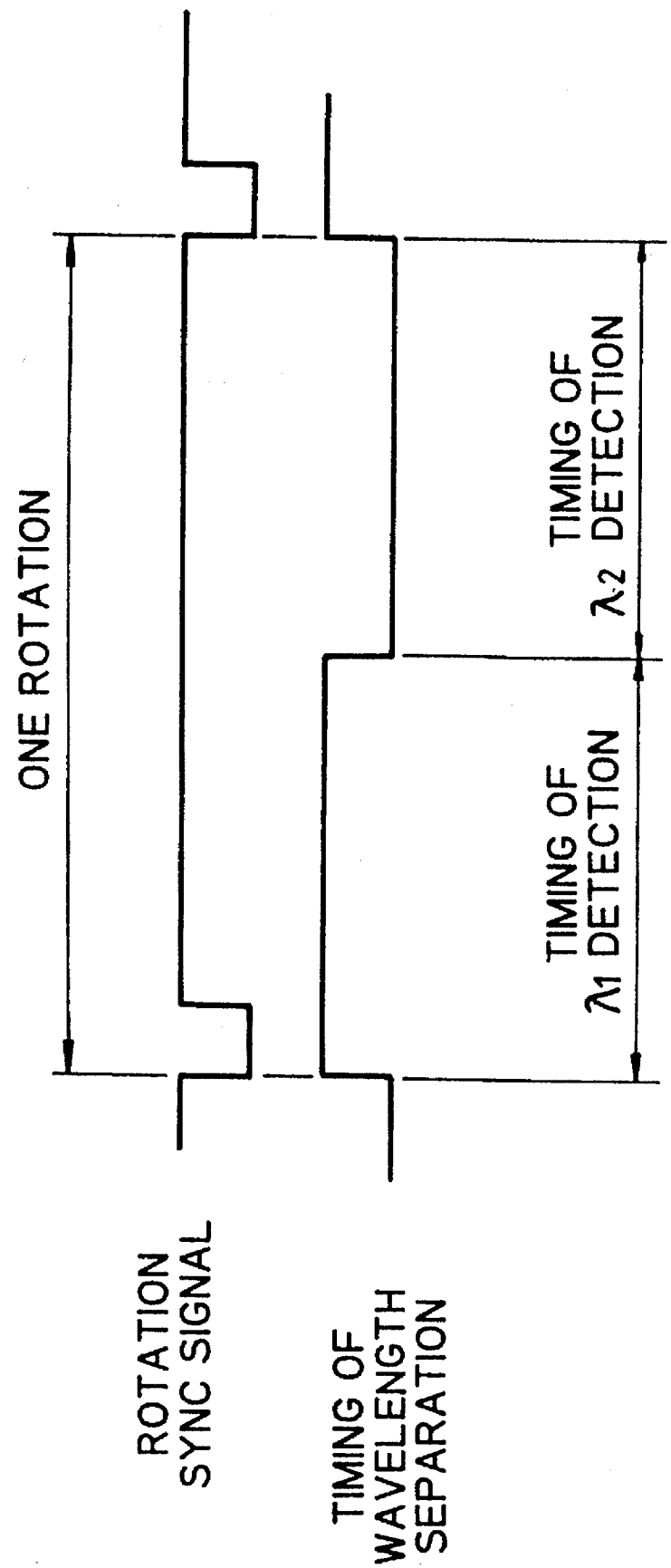
FIG. 18 is a timing chart showing the relationship between a rotation sync signal from the rotary filter shown in FIG. 17 and the timing of wavelength separation.

FIG. 12 shows schematically an example of the waveform of an output signal as produced from the CCD sensor 7 when it receives fluorescence. The positions of frames in the filtering thin film can be correlated to the positions of pixels in the CCD sensor if the same reference point is employed. For example, the fluorescence emitted from the Nth lane may be allotted in such a way that light of color A at wavelength λ1 corresponds to four pixels n, n+1, n+2 and n+3 whereas light of color B at wavelength λ2 corresponds to four pixels n+4, n+5, n+6 and n+7. Thusly, the numbers of pixels in the CCD sensor are predetermined in correspondence to the colors to be detected and a desired color can be separated on the basis of the relevant pixel numbers. Stated more specifically, if color portions at each of the wavelengths λ1 and λ2 are sampled, on the basis of pixel numbers, from the output signal waveform of the CCD sensor shown in FIG. 12 and synthesized again, the waveform for the light of color A at wavelength λ1 and that for the light of color B at wavelength λ2 are obtained independently of each other and these waveforms can be used to determine the respective bases A, T, C and G in the same manner as in the prior art. Thus, two kinds of specimens can be analyzed simultaneously in a single lane on a simple apparatus.

While the DNA base sequencer of the invention has been described above with reference to an embodiment that employs two fluorophores, it should be noted that the number of fluorescence markers that can be processed with the apparatus of the invention is in no way limited to two, but three or four fluorescence markers may be processed simultaneously. To this end, filtering thin films equal in number to the fluorescence markers to be used need be superposed in such a way that the windows in one film are staggered with respect to those in any adjacent film.

As described on the foregoing pages, the present invention provides a DNA base sequencer that achieves a sensitivity and resolution at least comparable to those attained by the prior art apparatus, and yet which is capable of detecting multi-color labelled samples by means of simpler detecting optics.

What is claimed is:

1. A DNA base sequencer, comprising a flat plate type gel electrophoretic means that has multiple tracks for electrophoresing DNA fragments and which is held in a vertical position, a light exciting laser light applying means that applies laser light to the respective tracks in said electrophoretic means from one lateral side thereof in such a way that it crosses said tracks at right angles, and a fluorescence detecting means that detects the fluorescence as generated from the DNA fragments illuminated with the laser light and which converts the detected fluorescence to an electric signal, the improvement wherein:

said fluorescence detecting means comprises a fluorescence condensing lens, fluorescence filtering means and a solid-state imaging device, said fluorescence filtering means being composed of at least two filters that selectively transmit fluorescences having difference wavelengths and that are staggered with each other along a common longitudinal axis;

wherein each of said filters comprises a dielectric multi-layered film coated on a transparent glass substrate and has multiple windows of the same shape and size formed on a straight line by removing selected areas of said film; and wherein said fluorescence filtering means is composed by superposing said filters in such a way that the windows in one film will not overlap those in the other film but are staggered with the latter.

2. A DNA base sequencer comprising a flat plate type gel electrophoretic means that has multiple tracks for electrophoresing DNA fragments and which is held in a vertical position, a light exciting laser light applying means that applies laser light to the respective tracks in said electrophoretic means from one lateral side thereof in such a way that it crosses said tracks at right angles, and a fluorescence detecting means that detects the fluorescence as generated from the DNA fragments illuminated with the laser light and which converts the detected fluorescence to an electric signal, the improvement wherein:

said fluorescence detecting means comprises a fluorescence condensing lens, fluorescence filtering means and a solid-state imaging device, said fluorescence filtering means being composed of at least two filters that selectively transmit fluorescences having difference wavelengths and that are staggered with each other along a common longitudinal axis;

wherein said fluorescence condensing lens is an index-distributed lens array and said solid-stage imaging device is a CCD line sensor.

3. A DNA base sequencer according to claim 2, wherein said index-distributed lens array consists of an upper and a lower row of index-distributed lenses.

4. A DNA base sequencer, comprising a flat plate type gel electrophoretic means that has multiple tracks for electrophoresing DNA fragments and which is held in a vertical position, a light exciting laser light applying means that applies laser light to the respective tracks in said electrophoretic means from one lateral side thereof in such a way that it crosses said tracks at right angles, and a fluorescence detecting means that detects the fluorescence as generated from the DNA fragments illuminated with the laser light and which converts the detected fluorescence to an electric signal, the improvement wherein:

said fluorescence detecting means comprises a fluorescence condensing lens, fluorescence filtering means and a solid-state imaging device, said fluorescence filtering means being composed of at least two filters that selectively transmit fluorescences having difference wavelengths and that are staggered with each other along a common longitudinal axis;

wherein said fluorescence detecting means comprises, in order from the electrophoretic means side, an index-distributed lens array, the fluorescence filtering means and a CCD line sensor.

5. A DNA base sequencer, comprising a flat plate type gel electrophoretic means that has multiple tracks for electrophoresing DNA fragments and which is held in a vertical position, a light exciting laser light applying means that applies laser light to the respective tracks in said electrophoretic means from one lateral side thereof in such a way that it crosses said tracks at right angles, and a fluorescence detecting means that detects the fluorescence as generated from the DNA fragments illuminated with the laser light and which converts the detected fluorescence to an electric signal, the improvement wherein:

said fluorescence detecting means comprises a fluorescence condensing lens, fluorescence filtering means and a solid-state imaging device, said fluorescence filtering means being composed of at least two filters that selectively transmit fluorescences having difference wavelengths and that are staggered with each other along a common longitudinal axis;

wherein said fluorescence detecting means comprises, in order from the electrophoretic means side, a first index-distributed lens array, the fluorescence filtering means, a second index-distributed lens array and a CCD line sensor.

6. A DNA base sequencer according to claim 3, wherein said CCD line sensor is cooled with Peltier devices.

* * * * *